United States Patent [19]

Litchfield et al.

[11] Patent Number: 4,582,804

[45] Date of Patent: Apr. 15, 1986

[54] MICROBIOLOGICAL SYNTHESIS OF HYDROXY-FATTY ACIDS AND KETO-FATTY ACIDS

[76] Inventors: John H. Litchfield, 255 Bryane Ave., Columbus, Ohio 43085; George E. Pierce, 6375 Hibiscus Ct., Westerville, Ohio 43081

[21] Appl. No.: 753,295

[22] Filed: Jul. 9, 1985

[51] Int. Cl.$^4$ .............................................. C12P 7/64

[52] U.S. Cl. .................................. 435/134; 435/132; 435/244; 435/253; 562/510

[58] Field of Search ............... 435/132, 134, 244, 253; 562/510

Primary Examiner—Paul R. Michl
Assistant Examiner—Alex H. Walker

[57] ABSTRACT

The synthesis of hydroxy-fatty acids and keto-fatty acids from unsaturated fatty acids by *Rhodococcus rhodochrous* is disclosed.

19 Claims, No Drawings

MICROBIOLOGICAL SYNTHESIS OF HYDROXY-FATTY ACIDS AND KETO-FATTY ACIDS

FIELD OF THE INVENTION

The invention relates to the biosynthesis of hydroxy-fatty acids and keto-fatty acids from unsaturated fatty acids by the microorganism.

BRIEF DESCRIPTION OF THE PRIOR ART

Microbiological processes have long been of commercial importance. The chemical compounds that are manufactured by such processes range greatly in structure and complexity and include medically valuable antibiotics as well as simple compounds used as starting materials in the synthesis of other compounds.

The present invention describes a microbiological process of synthesis of hydroxy-fatty acids and keto-fatty acids from unsaturated fatty acids, such as linoleic or oleic acids, or mixtures of unsaturated fatty acids. One of the products of this process is 10-hydroxy-12-octadecenoic acid. This compound is a geometric isomer of ricinoleic acid, an important material used in the production of sebacic acid. The latter is used commercially in the synthesis of resins. At present, ricinoleic acid is largely derived from castor beans, where it is the major fatty acid of the castor oil.

Prior to this invention, the microbiological synthesis of ricinoleic acid had been reported by a research group in the United Kingdom. Morris, et al. described in Biochem. J., 100; 296-316 (1966), the synthesis of ricinoleic acid by the mycelium of the pathogenic fungus *Claviceps purpurea*. The ricinoleic acid is synthesized by this organism from linoleic acid. This biosynthetic reaction is apparently a hydration rather than an oxidation and is analogous to the formation of D-10-hydroxystearic acid by Pseudomonas sp. described by Wallen, et al. in Lipids, 6: 745-750 (1971). The same species can hydrate a number of other unsaturated fatty acids. All of these reactions required anaerobic conditions.

*Nocardia opaca* and *Nocardia restrictus* have been reported able to hydrate cyclic olefins. For a review of microbial hydroxylations, see Fonken and Johnson in "Chemical Oxidations with Microorganisms," Marcel Dekker, New York (1972). There are no known reports of this organism's ability to hydrate straight chain olefins.

The present invention is an improvement over the prior art. *Rhodococcus rhodochrous*, previously known as *Nocardia aurantia*, is not a pathogen; this is in contrast to *Claviceps purpurea*. There are no difficulties in culturing and using *R. rhodochrous* on a commercial scale. A further advantage is that it does not require use under anaerobic conditions, which are difficult to maintain. Furthermore, *R. rhodochrous* is easy to cultivate using inexpensive, readily available nutrients.

SUMMARY OF THE INVENTION

The invention comprises a process for the synthesis of a hydroxy fatty acid, which comprises; hydration of an unsaturated fatty acid by the microorganism [Rhodococcus rhodochrous.

In a preferred embodiment, linoleic or oleic acids are transformed to hydroxy fatty acids. With linoleic acid as the substrate, 10-hydroxy-12-octadecenoic acid, an isomer of ricinoleic acid, is produced. Co-produced with the hydroxy fatty acids are keto-fatty acids. In the case of linoleic acid substrate, 10-keto-12-octadecenoic acid is also produced. With oleic acid as the substrate, 10-hydroxystearic and 10-kerosstearic acids are synthesized. The 10-hydroxystearic acid is useful for all of the purposes associated with the commercially valuable 12-hydroxystearic acid.

The process of the invention offers a number of advantages over the prior art. For example, the biotransformation may be carried out under aerobic conditions. Aerobic conditions are much easier to maintain than anaerobic conditions, where air has to be evacuated and replaced with an inert gas.

DETAILED DESCRIPTION OF THE PREFERRED EMBODIMENTS OF THE IMVENTION

The process of this invention is based on the discovery that the microorganism *Rhodococcus rhodochrous* can convert unsaturated fatty acids to hydroxy-fatty acids. This is accomplished by the mechanism of hydration, whereby a hydrogen atom and a hydroxyl group are added to the two adjacent carbons of the olefinic bond. Coproduced in the process of this invention are corresponding keto-fatty acids, which might be made by oxidation of the hydroxy fatty acids. This oxidation is presumed to be catalyzed by enzyme(s) present in association with the *R. rhodochrous*.

In a preferred embodiment of this invention, the microorganisms are first subjected to a period of growth in the presence of an inducing substance. The induction period allows the enzyme or enzymes necessary to the biotransformation to be made available. The inducer can be the same substance as the substrate from which the desired product is formed, or it can be some other compound. In one embodiment, both the substrate and the inducer are oleic acid. In another embodiment, the inducer is oleic acid and the substrate is linoleic acid.

When linoleic acid is used as the substrate and oleic acid is used as the inducer, the major product formed by *Rhodococcus rhodochrous* is 10-hydroxy-12-octadecenoic acid of the formula:

This compound, an isomer of ricinoleic acid, has been obtained in as much as about 50% yield from the reacted linoleic acid. Another compound formed from linoleic acid is 10-keto-12-octadecenoic acid. Other products from the reaction using linoleic acid as substrate and oleic acid as inducer are 10-hydroxystearic acid and 10-ketostearic acid.

When oleic acid is used as the substrate with either oleic or linoleic acid as the inducer, 10-hydroxystearic and 10-ketostearic acids are obtained. Again, it is oleic acid that is the more effective inducer. As much as 96% of the initial substrate may be transformed, of which about 60% is 10-hydroxystearic acid.

For the biotransformation to be most effective, the cells of *Rhodococcus rhodochrous* should be freshly prepared, although this is not critical to the process of the invention. The use of fresh cells obviates the presence of toxic waste products of the cells. Fresh preparations of the microorganisms may be obtained by first inoculating a stock culture [maintained in yeast extract-malt extract agar (YEMEA) at 26° C.] onto fresh YEMEA and incubating overnight at a temperature of 26° C. The resulting culture is used to inoculate flasks containing YEMEA broth. These flasks are then incubated for 18 hours at a temperature of 26° C.

When employed, the inducing substance is added to the flasks of fresh cell culture, following the last mentioned incubation. The inducing substance is added 0.1 to 1.0 mg/ml; preferably 0.5 mg/ml, and the cultures are incubated an additional 20–24 hours at temperature of 26° C. At the end of the induction period, the cells are harvested by centrifugation and resuspended, concentrated in fresh Stainer's medium containing 2% yeast extract.

The concentration step allows for easier extraction of the subsequently produced hydroxy fatty acids from the added substrate.

The cells of R. rhodochrous are brought together with the unsaturated fatty acid substrate, preferably after induction as described above. In a preferred embodiment, 20 to 100 mg (preferably circa 60 mg) of the substrate is added to 3 ml. of a 20-fold concentrate of the cells. The resulting mixture may then be incubated at room temperature until the desired product is obtained. Typically, incubation at a temperature of circa 26° C. provides the desired product within about 24 hours. Process of the desired biotransformation may be followed by periodic analysis of the incubating mixture for presence of the desired product.

At the end of the incubation time, the cultures are centrifuged to remove the cellular material, and the reaction media (supernatant) is removed. The cellular material is resuspended in fresh reaction media, centrifuged and the supernatant combined with the previous supernatant. The cellular material is then resuspended in acidified distilled water and the cell suspension may be extracted by one of several solvent extraction techniques. A preferred extraction is with one or more extractions using a solvent for the product, such as ether. The solvent extracts are combined with the reaction media supernatants. The combined solvent extracts and supernatants are then acidified, preferably with 6N HCl and extracted a plurality of times with anhydrous solvents. The solvent extracts are combined, dried and stripped of solvent to obtain the desired products.

The following examples illustrate the manner and process of making and using the invention and set forth the best mode of carrying out the inventions but they are not to be construed as limiting.

PREPARATION 1

STAINER'S MEDIUM PLUS YEAST EXTRACT

Stainer's medium is prepared by admixture of:
40 ml of $Na_2HPO_4 + KH_2PO_4$ Buffer (pH 6.8)
20 ml of Hutner's vitamin-free mineral base
1000 ml Distilled $H_2O$
1.0 g $(NH_4)_2SO_4$ (add last)
To above medium add yeast extract to a final concentration of 2%.

The Hutner's mineral base is prepared by admixture of:

| | |
|---|---|
| Nitrilotriacetic acid | 10.0 g |
| $MgSO_4$ | 14.45 g |
| $CaCl_2.2H_2O$ | 3.335 g |
| $(NH_4)_6Mo_7O_{24}.4H_2O$ | 0.00925 g |
| $FeSO_4.7H_2O$ | 0.099 g |
| Stock Salt Soln. | 50 ml |
| Distilled $H_2O$ | 950 ml |

Dissolve nitrolotriacetic acid in distilled $H_2O$ neutralized with 7.3 g KOH. The stock salt solution used in the preparation of the Hutner's mineral base is a mixture of:

| | |
|---|---|
| ethylene diamine tetraacetic acid (EDTA) | 2.5 g |
| $ZnSO_4.7H_2O$ | 10.95 g |
| $FeSO_4.7H_2O$ | 5.0 g |
| $MnSO_4.7H_2O$ | 1.54 g |
| $CuSO_4.5H_2O$ | 0.392 g |
| $Co(NO_3)_2.6H_2O$ | 0.248 g |
| $Na_2B_4O_7.10H_2O$ | 0.177 g |
| Distilled $H_2O$ | 1000 ml |

Add several drops of $H_2SO_4$ to reduce precipitation.

PREPARATION 2

YEAST EXTRACT-MALT EXTRACT BROTH (YEMEB) and AGAR (YEMEA)

The composition of yeast extract-malt extract (YEMEB) is:

| | |
|---|---|
| Yeast Extract | 4 g |
| Malt Extract | 10 g |
| Glucose | 4 g |
| Distilled $H_2O$ | 1.0 l |

For YEMEA, add the YEMEB to Agar, use 2% (20 g/l) Bacto Agar (Difco).

PREPARATION 3

R. rhodochrous cell culture

*Rhodococcus rhodochrous* ATCC 12674 (previously known as *Nocardia aurantia*) is maintained on yeast extract-malt extract agar (YEMEA) at 20° C. The cells for transformation are grown in yeast extract-malt broth (YEMEB). Both linoleic and oleic acids supported growth of *R. rhodochrous* equally well when incorporated into either Stainer's minimal medium or Stainer's medium plus 2% yeast extract. To prepare fresh cells for the process of the invention, the maintained cells are processed as follows:

(1) Grow *Rhodococcus rhodochrous* in yeast extract-malt extract agar (YEMEA) overnight.
(2) Use culture from (1) above to inoculate 500 ml flasks containing 200 ml YEMEA and incubate for 18 hours at 20° C.
(3) Add inducer (oleic or linoleic acid) at 0.5 mg/ml and incubate additional 22–24 hours at 26° C.
(4) Harvest cells by centrifugation (8,000 rpm for 15 minutes).
(5) Resuspended cells in Stainer's medium+2% yeast extract (YE) (to give a 20X concentration of cells).

EXAMPLE 1

*Rhodococcus rhodochrous* with Linoleic Acid as Substrate

An appropriate vessel is charged with 3.0 ml of the concentrated cell suspension of Preparation 3, supra, wherein the inducing substance was oleic acid. To the charge there is added 60 mg of linoleic acid. The mixture is incubated for 24 hours at a temperature of 26° C.

At the end of this period of time the mixture is centrifuged to remove the cellular material and the reaction media (supernatant) is removed. The cellular material is resuspended in fresh reaction media, centrifuged and the supernatant combined with the previous supernatant. The cellular material is then resuspended in acidified distilled water and the cell suspension is extracted twice with ether. The ether extracts are combined with the reaction media supernatants.

The combined ether extracts and supernatants are then acidified with 6N HCl and extracted three times with anhydrous ether. The ether extracts are combined and passed through a funnel packed with anhydrous $Na_2SO_4$ to remove residual water. The partially dried material is taken to near dryness via removing the ether on a flash evaporator. The near-dried material is transferred to a scintillation via and the remaining ether is evaporated off under a $N_2$ purge. The material is then placed in a $P_2O_5$ dessicator to remove the last traces of water. To monitor the efficiency of the extraction procedure, heptadecanoic acid is added to the material prior to the initial acidification and extraction steps.

The extracted materials are then methylated with diazomethane and isolated by gas chromotography using known procedures. Products are identified by gas chromotography and mass spectroscopy. The position of the double bond is confirmed by ozonolysis. The product of this example 1, is 13.3 mg of 10-hydroxy-12-octadecenoic acid (22.2% yield; 46.5% selectivity).

EXAMPLE 2

*Rhodococcus rhodochrous* with Oleic Acid as a Substrate

The procedure of Example 1, supra., is repeated except that the linoleic acid as used therein is replaced with an equal weight of oleic acid. The products, 10-ketostearic acid and 10-hydroxystearic acid, are obtained as follows:

|  | 10-Ketostearic Acid | 10-Hydroxystearic Acid |
|---|---|---|
| Amount formed (mg): | 7.4 | 33.1 |
| % Selectivity: | 12.9 | 57.6 |
| % Yield: | 12.3 | 55.7 |

What is claimed:

1. A process for the synthesis of a hydroxy fatty acid, which comprises;
   hydration of a first unsaturated fatty acid by the microorganism *Rhodococcus rhodochrous*.
2. The process of claim 1 wherein the unsaturated fatty acid is oleic acid.
3. The process of claim 1 wherein the unsaturated fatty acid is linoleic acid.
4. The process of claim 1 wherein the microorganism is first subjected to an induction period with an inducer, said inducer being a second unsaturated fatty acid.
5. The process of claim 4 wherein the inducer is oleic acid.
6. The process of claim 5 wherein the first fatty acid is linoleic acid.
7. The process of claim 5 wherein the first fatty acid is oleic acid.
8. The process of claim 4 wherein the inducer is linoleic acid.
9. The process of claim 8 wherein the first fatty acid is linoleic acid.
10. The process of claim 8 wherein the first fatty acid is oleic acid.
11. The process of claim 4 wherein the inducer is added to 0.5 mg/ml.
12. The process of claim 4 wherein the induction period is 20–24 hours at room temperature.
13. The process of claim 4 wherein the microorganism is provided in a fresh culture.
14. The process of claim 13 wherein the microorganism cells are concentrated after induction.
15. The process of claim 14 wherein the cells are concentrated 20-fold.
16. The process of claim 14 wherein the proportion of first acid added is 60 mg to 3 ml of cell concentrate.
17. The process of claim 16 wherein the cells are incubated with the first acid for 24 hours at room temperature.
18. The process of claim 1 wherein a keto-fatty acid is coproduced with the hydroxy-fatty acid.
19. The process of claim 1 wherein said unsaturated fatty acid comprises a mixture of unsaturated fatty acids.

* * * * *